(12) United States Patent
Backman et al.

(10) Patent No.: US 6,624,890 B2
(45) Date of Patent: Sep. 23, 2003

(54) POLARIZED LIGHT SCATTERING SPECTROSCOPY OF TISSUE

(75) Inventors: Vadim Backman, Cambridge, MA (US); Ramachandra R. Dasari, Lexington, MA (US); Rajan Gurjar, Cambridge, MA (US); Irving Itzkan, Boston, MA (US); Lev Perelman, Brookline, MA (US); Michael S. Feld, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 10/155,194

(22) Filed: May 24, 2002

(65) Prior Publication Data

US 2002/0171831 A1 Nov. 21, 2002

Related U.S. Application Data

(63) Continuation of application No. 09/237,153, filed on Jan. 25, 1999, now Pat. No. 6,404,497.

(51) Int. Cl.[7] .................................................. G01J 4/00
(52) U.S. Cl. ....................................................... 356/369
(58) Field of Search ................................ 356/364, 365, 356/369; 600/160

(56) References Cited

U.S. PATENT DOCUMENTS

| 3,675,768 A | 7/1972 | Legorreta-Sanchez ........ 209/4 |
| 4,281,931 A | 8/1981 | Chikama .................... 356/372 |
| 4,336,809 A | 6/1982 | Clark ........................ 128/665 |

(List continued on next page.)

FOREIGN PATENT DOCUMENTS

| DE | 4343663 | 4/1995 |
| EP | 351 659 B1 | 1/1990 |
| EP | 670 496 B1 | 10/1995 |
| JP | 62116263 | 5/1987 |
| JP | 05203564 | 8/1993 |
| WO | WO 92/14399 | 9/1992 |
| WO | WO 96/28084 | 9/1996 |
| WO | WO 96/29926 | 10/1996 |
| WO | WO 98/38907 | 10/1998 |
| WO | WO 99/18845 | 4/1999 |

OTHER PUBLICATIONS

Newton, R.G., Scattering Theory of Waves and Particles, Second Edition, Chapter 2, "Sperically Symmetric Scatterers", pp. 30–53. Chapter 3, "Limiting Cases and Approximations", pp. 54–78.

Perelman et al., "Observation of Periodic Fine Structure in Reflectance from Biological Tissue: A New Technique for Measuring Nuclear Size Distribution", *Amer. Phys. Society*, vol. 80, No. 3 (Jan. 19, 1998), pp. 627–630.

Mourant et al., "Mechanisms of Light Scattering from Biological Cells Relevant to Noninvasive Optical–tissue Diagnostics", *Applied Optics*, vol. 38, No. 16 (Jun. 1, 1998), pp. 3586–3593.

Brunsting, et al., "Differential Light Scattering From Spherical Mammalian Cells", *Biophys. J.*, vol. 14 (1974), pp. 439–453.

Riddell et al., "Dysplasia in Inflammatory Bowel Disease", *Human Pathology*, vol. 14, No. 11 (Nov., 1983), pp. 931–968.

Atkin et al., "Long–Term Risk of Colorectal Cancer After Excision of Rectosigmoid Adenomas", *New England J. Med.*, vol. 326, No. 10 (Mar. 5, 1992), pp. 658–662.

R. Rox Anderson, MD, "Polarized Light Examination and Photography of the Skin", *Arch Dermatol*, vol. 127 (Jul., 1991), pp. 1000–1005.

*Primary Examiner*—Michael P. Stafira
(74) *Attorney, Agent, or Firm*—Bowditch & Dewey LLP

(57) ABSTRACT

The present invention relates to the use of polarized light to measure properties of tissue. More particularly, polarized light can be used to detect dysplasia in tissue as the polarization of back-scattered light from such tissues is preserved while the contribution of diffusely scattered light from underlying tissues can be removed. A fiber optic system for delivery and collection of light can be used to measure tissues within the human body.

19 Claims, 7 Drawing Sheets

U.S. PATENT DOCUMENTS

| | | | |
|---|---|---|---|
| 4,515,165 A | 5/1985 | Carroll | 128/664 |
| 4,625,167 A | 11/1986 | Fitzpatrick | 324/235 |
| 4,655,225 A | 4/1987 | Dähne et al. | 128/633 |
| 4,699,512 A | 10/1987 | Koshi | 356/318 |
| 4,718,417 A | 1/1988 | Kittrell et al. | 128/303.1 |
| 4,768,513 A | 9/1988 | Suzuki | 128/634 |
| 4,802,760 A | 2/1989 | Inoue et al. | 356/31 |
| 4,829,184 A | 5/1989 | Nelson et al. | 250/358.1 |
| 4,884,886 A | 12/1989 | Salzman et al. | 356/367 |
| 4,948,974 A | 8/1990 | Nelson et al. | 250/358.1 |
| 4,953,978 A | 9/1990 | Bott et al. | 356/336 |
| 4,988,199 A | 1/1991 | Paul | 356/368 |
| 5,014,709 A | 5/1991 | Bjelkhagen et al. | 128/654 |
| 5,061,075 A | 10/1991 | Alfano et al. | 356/417 |
| 5,106,387 A | 4/1992 | Kittrell et al. | 606/15 |
| 5,168,162 A | 12/1992 | Oong et al. | 250/339 |
| 5,280,788 A | 1/1994 | Janes et al. | 128/665 |
| 5,284,137 A | 2/1994 | Kessler et al. | 128/633 |
| 5,290,275 A | 3/1994 | Kittrell et al. | 606/15 |
| 5,303,026 A | 4/1994 | Strobl et al. | 356/318 |
| 5,309,907 A | 5/1994 | Fang et al. | 128/633 |
| 5,313,264 A | 5/1994 | Ivarsson et al. | 356/73 |
| 5,317,156 A | 5/1994 | Cooper et al. | 250/345 |
| 5,333,052 A | 7/1994 | Finarov | 356/369 |
| 5,345,306 A | 9/1994 | Ichimura et al. | 356/346 |
| 5,369,496 A | 11/1994 | Alfano et al. | 356/446 |
| 5,386,827 A | 2/1995 | Chance et al. | 128/633 |
| 5,398,685 A | 3/1995 | Wilk et al. | 128/653.1 |
| 5,402,778 A | 4/1995 | Chance | 128/633 |
| 5,418,136 A | 5/1995 | Miller et al. | 435/5 |
| 5,419,321 A | 5/1995 | Evans | 128/633 |
| 5,434,669 A * | 7/1995 | Tabata et al. | 356/241.5 |
| 5,440,388 A | 8/1995 | Erickson | 356/346 |
| 5,452,723 A * | 9/1995 | Wu et al. | 250/339.01 |
| 5,460,177 A | 10/1995 | Purdy et al. | 128/633 |
| 5,491,344 A | 2/1996 | Kenny et al. | 250/461.1 |
| 5,494,829 A | 2/1996 | Sandstrom et al. | 436/518 |
| 5,560,356 A | 10/1996 | Peyman | 128/633 |
| 5,582,168 A | 12/1996 | Samuels et al. | 128/633 |
| 5,582,169 A | 12/1996 | Oda et al. | 128/633 |
| 5,596,987 A | 1/1997 | Chance | 128/633 |
| 5,596,992 A | 1/1997 | Haaland et al. | 128/664 |
| 5,625,458 A | 4/1997 | Alfano et al. | 356/446 |
| 5,630,423 A | 5/1997 | Wang et al. | 128/664 |
| 5,636,633 A | 6/1997 | Messerschmidt et al. | 128/633 |
| 5,640,247 A | 6/1997 | Tsuchiya et al. | 356/446 |
| 5,784,162 A | 7/1998 | Cabib et al. | 356/346 |
| 5,813,987 A | 9/1998 | Modell et al. | 600/473 |
| 5,938,617 A | 8/1999 | Vo-Dinh | 600/476 |
| 6,002,480 A | 12/1999 | Izatt et al. | 356/345 |
| 6,011,626 A | 1/2000 | Hielscher et al. | 356/367 |
| 6,091,984 A | 7/2000 | Perelman et al. | 600/476 |
| 6,177,984 B1 * | 1/2001 | Jacques | 356/338 |
| 6,404,497 B1 | 6/2002 | Backman et al. | 356/369 |

\* cited by examiner

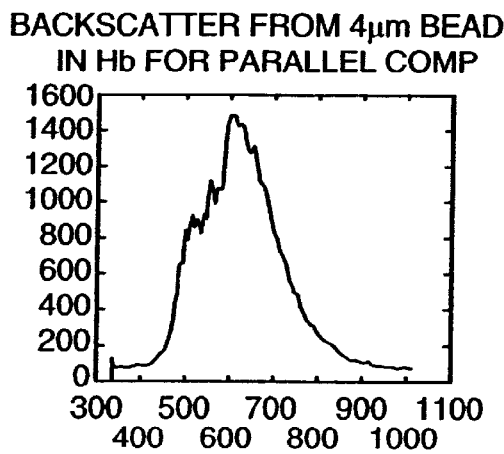
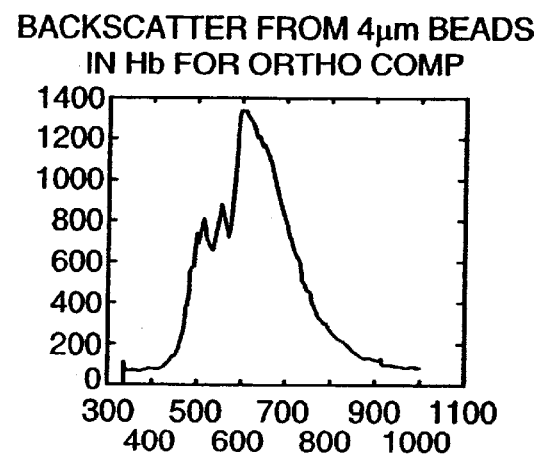
FIG. 2A      FIG. 2B
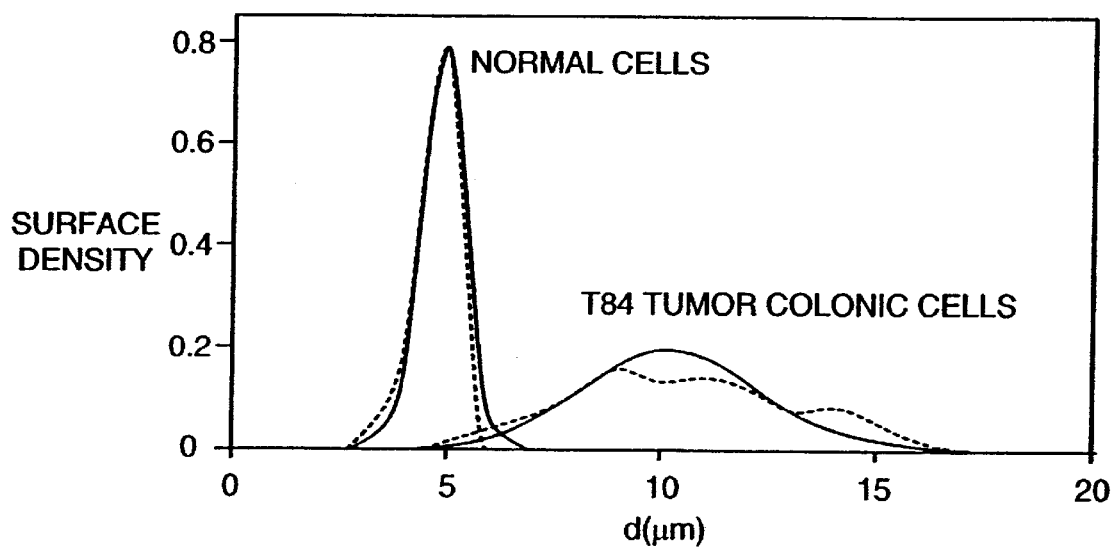
FIG. 6

POLARIZED LIGHT SCATTERING SPECTROSCOPY OF TISSUE

CROSS REFERENCES TO RELATED APPLICATIONS

The present application is a continuation application of U.S. patent application Ser. No. 09/237,153, filed Jan. 25, 1999, now U.S. Pat. No. 6,404,497.

The entire contents of the above application is incorporated herein by reference in entirety.

GOVERNMENT SUPPORT

This invention was supported, in whole or in part, by a grant number P41RR02954 from National Institute for Health. The Government has certain rights in the invention.

BACKGROUND OF THE INVENTION

More then 90% of cancer lesions are epithelial in origin. Several of the most common forms of epithelial cancers such as colorectal, esophageal, bladder, cervical and oral cancers have a well defined, detectable pre-cancer stage called dysplasia. Dysplasia is characterized by sequential accumulation of mutations in defined oncogenes and tumor suppresser genes. If detected, the absolute majority of the dysplastic lesions are curable. Clinical efforts to detect and treat this pre-cancerous stage of epithelial cancer have been shown to reduce the mortality rate.

Diagnosis of epithelial dysplasia remains difficult because it typically does not form macroscopic structures such as polyps, and is usually only visible after cancer has developed. Standard methods of detecting epithelial dysplasia are based on random biopsies and pathologic examination of the stained biopsy material. However, random biopsies have high sampling error. In many cases less than 1% of the epithelial surface at risk for dysplasia can be examined.

All types of epithelial dysplasia have several common characteristics, namely enlargement of epithelial cell nuclei with an increase in the nuclear to cytoplasmic ratio, nuclear hyperchromatism, and increased number and stratification of epithelial cells. Despite these well-characterized epithelial changes, classification has been difficult as demonstrated by high inter-observer disagreement, even among experienced pathologists.

SUMMARY OF THE INVENTION

Non-invasive, in-vivo methods of detecting epithelial dysplasia provide for surveillance of epithelial surfaces, and the pathological diagnosis of pre-cancerous conditions in humans.

Optical techniques are well suited to be a substitution for random biopsies, since they are non-invasive, do not require tissue removal, and can be performed in-vivo. Moreover, they are fast (can be applied in real time), are relatively non-expensive, are able to work on microscopic scale, and thus can find very small dysplastic sites. The latter are highly likely to be missed by random biopsies.

The present invention relates to light scattering spectroscopy of polarized light to provide information about scatterers in surface layers of turbid media such as tissue. This process need not utilize fluorescence or absorption spectral features, but rather scattering properties of surface tissues such as epithelial layers. It can characterize properties of large scatterers (cell nuclei) in human epithelium and provide histological information about human tissues and diagnose dysplasia in real time in human organs in-vivo.

The idea of light scattering spectroscopy of unpolarized light to determine features of epithelial tissue has been described in U.S. Ser. No. 08/948,734 filed on Oct. 10, 1997, and in International Application No. PCT/US98/21450 filed on Oct. 9, 1998, which designated the United States, the entire contents of these applications being incorporated herein by reference. The major centers of light scattering in epithelium are cellular organelles such as mitochondria and nuclei with the refractive index higher than that of the surrounding cytoplasm. Light backscattered from surface epithelial cell nuclei has an oscillatory wavelength dependent component. The periodicity of this component increases with nuclear size, and its amplitude is related to the density of the nuclei. Thus, by analyzing the amplitude and frequency of the oscillatory component, the density and size distribution of epithelial nuclei can be determined. Normal nuclei have a characteristic diameter l=4–7 $\mu$m. In contrast, dysplastic nuclei can be as large as 20 $\mu$m. Nuclear size and density are important indicators of neoplastic precancerous changes in biological tissue. The ability to measure nuclear size distribution in vivo and in real time has valuable applications in clinical medicine. This enables the diagnosis of precancerous changes in various human organs such as esophagus, colon, bladder, oral cavity, cervix, etc. non-invasively and in real-time.

Epithelium covers surfaces of organs in the human body. The thickness of epithelium ranges from 20 $\mu$m (one cell layer) to a few hundred microns (multiple cell layers). Beneath epithelium there are layers of relatively acellular connective and muscular tissues. Since dysplasia is limited to the epithelium, it is important to differentiate between the signal associated with the epithelium and underlying tissues. The backscattered component which carries information about surface epithelial nuclei is present in light reflected from mucosal tissues. However, it is ordinarily very small in amplitude, and easily masked by a background signal formed by diffuse scattering from the underlying tissue. To analyze that component the background signal must be removed. One can remove the diff-use background by modeling the general spectral features of the background. However, to make the approach more useful in practical medicine, and to be able to diagnose dysplasia in vivo, in real time, and in different organs, it is necessary to develop more robust method of removing or significantly reducing the diffuse component of the scattered light.

The present invention provides a method of measuring scattering features of epithelial cells by using polarized light spectroscopy. Note that initially polarized light looses its polarization while traveling through a turbid medium (tissue is an example of turbid medium). On the other hand the light scattered backward after a single scattering preserves polarization. Thus, by removing the nonpolarized component of the scattered light, one is able to distinguish light scattered by epithelial cells. The residual spectrum can be further analyzed so that the size distribution of the nuclei and their density can be determined.

A preferred embodiment of the inventions includes a fiber optic light delivery and collection system for diagnoses of tissue. The fiber optic system can be housed in a probe housing proximal and distal ends where the distal end can be inserted into the various lumens of the human body for in vivo measurements of tissue. Polarizers can be used on the distal ends of both delivery and collection fibers. With optical fibers that preserve the polarization of light, the polarizers can be positioned at the proximal end of the probe. In a three fiber system, the probe can use a central delivery fiber and two off-center collection fibers that collect two different polarization components of light returning from the tissue. The polarizers can be birefringent crystalline materials such as quartz, sapphire or calcite. The calcite must be sealed from the working environment.

BRIEF DESCRIPTION OF THE DRAWINGS

FIGS. 2A and 2B are reflectance spectra of the two-layered tissue phantom (polystyrene beads on top of gel containing blood and $BaSO_4$) for parallel and perpendicular polarizations (notice characteristic hemoglobin dips), respectively.

FIG. 6 shows the nuclear size distribution for normal intestinal cells and T84 cancerous colonic cells where in each case, the solid line is the distribution extracted from the data, and the dashed line is the distribution measured using light microscopy.

Figure 1:
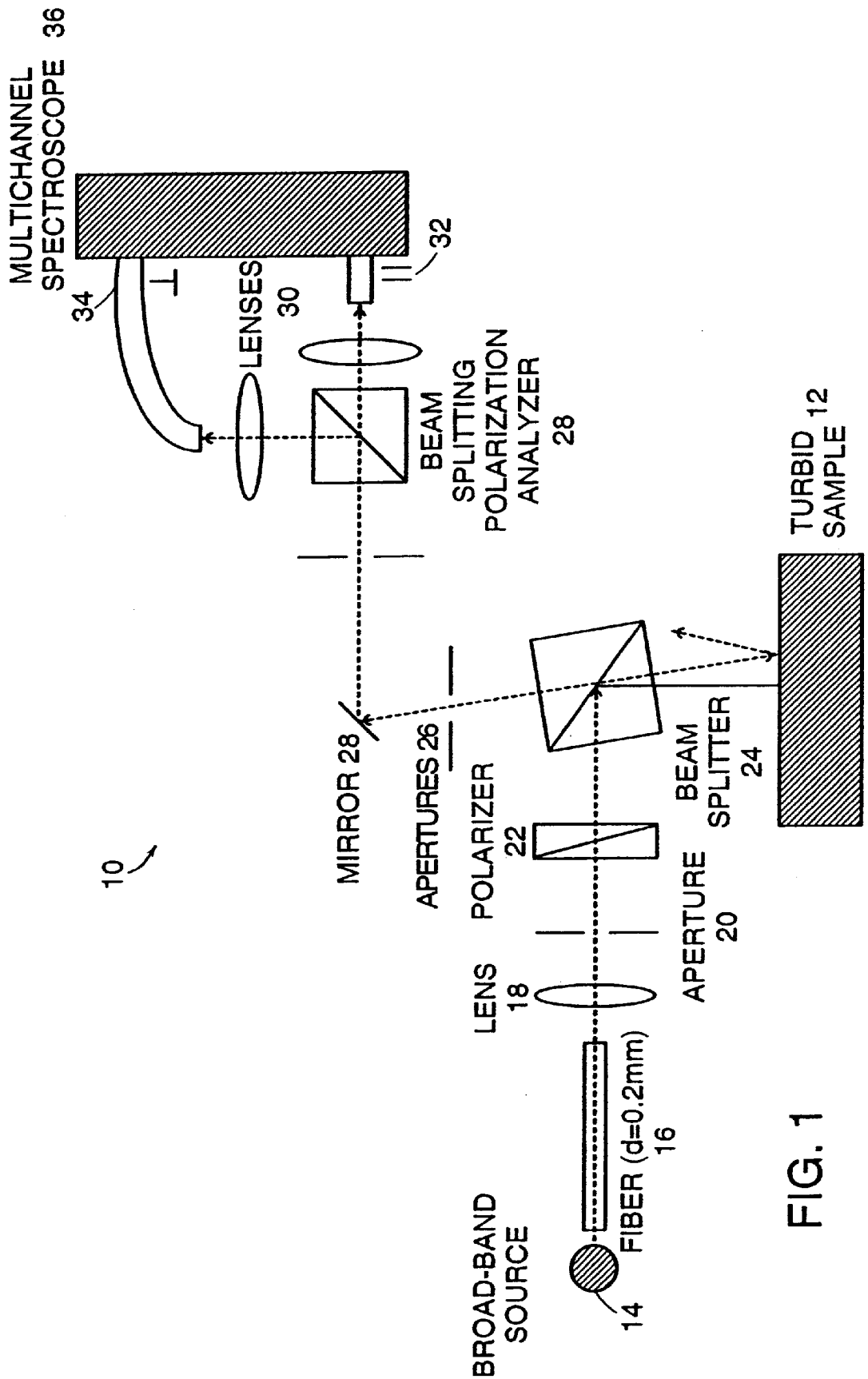
FIG. 1 illustrates a preferred embodiment of a polarization-based light scattering spectroscopic system.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, with emphasis being placed upon illustrating the principles of the invention.

DETAILED DESCRIPTION OF THE INVENTION

To determine properties of epithelial cells, one can correlate measured spectrum of the backscattered light with a model or representation. Using Mie theory, which provides the exact solution for the problem of light scattering by spherical objects of arbitrary sizes, the sizes and relative refractive indexes of the scatterers can be determined.

For polarized incident light, light scattered by a spherical particle with diameter d has components which are polarized parallel and perpendicular to the plane of scattering. For a plane polarized wave incident in direction $\hat{s}_0$, light scattered into direction $\hat{s}$ will have components which are polarized parallel (p) and perpendicular (s) to the plane of scattering. Intensities $I_p$ and $I_s$ of these components are related to the intensities of the incident light $I_p^{(0)}$ and $I_s^{(0)}$ as follows:

$$I_p(\hat{s}) = 4\frac{|S_2(\hat{s}, \hat{s}_0)|^2}{K^2 d^2} I_p^0(\hat{s}_0) \qquad (1)$$

$$I_s(\hat{s}) = 4\frac{|S_2(\hat{s}, \hat{s}_0)|^2}{K^2 d^2} I_p^0(\hat{s}_0) \qquad (2)$$

where k is the wavenumber of the incident light, $S_1$ and $S_2$ are scattering amplitudes which can be calculated numerically using Mie theory, and $s_1$ and $s_2$ are unit vectors defining propagation of the incident and scattered light. Scattering amplitudes are functions of a scattering angle $I=\cos^{-1}(s \cdot s_0)$ and are normalized so that integral $$\int_0^\pi (|S_1(\vartheta)|^2 + |S_2(\vartheta)|^2) \sin\vartheta \, d\vartheta$$

equals the total elastic scattering cross section.

Now consider an experiment in which linearly polarized incident light, intensity $I_0$, is distributed over solid angle $\Delta\Omega_0$ and scattering is collected over solid angle $\Delta\Omega$. The polarization, $\hat{\epsilon}_0$, of the incident light can be decomposed into a component $\hat{\epsilon}_p^0$, in the scattering plane (i.e. the plane formed by $\hat{s}$ and $\hat{s}_0$) and a perpendicular component $\hat{\epsilon}_s^0$. By means of analyzers, we detect two orthogonal components of the scattered light intensity, I∥ having polarization $\hat{\epsilon}'_a$ and $I_\perp$ having perpendicular polarization $\hat{\epsilon}''_a$. The scattered intensity components are then given by $$I_\| = \qquad (3)$$
$$\frac{2}{\pi k d^2}\int_{\Delta\Omega} d\hat{s} \int_{\Delta\Omega} d\hat{s}_0 I_0(\hat{s}_0)|S_2(\hat{s}_0, \hat{s})\cos\varphi\cos\varphi_0 + S_1(\hat{s}_0, \hat{s})\sin\varphi\sin\varphi_0|^2$$

$$I_\perp = \qquad (4)$$
$$\frac{2}{\pi k d^2}\int_{\Delta\Omega} d\hat{s} \int_{\Delta\Omega} d\hat{s}_0 I_0(\hat{s}_0)|S_2(\hat{s}_0, \hat{s})\cos\varphi\sin\varphi_0 - S_1(\hat{s}_0, \hat{s})\sin\varphi\cos\varphi_0|^2$$

If the incident light is completely collimated ($\Delta\Omega_0=0$) light scattered directly backward ( ) will be polarized parallel to the incident light polarization. In this case we can orient one of the analyzers parallel to the incident polarization direction ($\hat{\epsilon}_0 \approx \hat{\epsilon}'_a$). If the solid angles of the incident and collected light are sufficiently small and approximately equal, both $I_\|$ and $I_\perp$ will be present. However, the analyzer can still be positioned such that ($\hat{\epsilon}_0 \approx \hat{\epsilon}'_a$). Thus, in this case the collected light will still be highly polarized, and $I_\| \gg I_\perp$. For this case the expression for the residual intensity, $I_{81} - I_\perp$ can be simplified:

$$I_\| - I_\perp \approx \frac{4 I_0}{kd^2}\int_0^{\vartheta_0} \mathrm{Re}(S_1^*(\vartheta)S_2(\vartheta))\sin\vartheta \, d\vartheta, \quad \text{with } \vartheta_0 = \sqrt{\frac{\Delta\Omega}{2\pi}}. \qquad (5)$$

Consider a system of two layers of scattering media such as epithelial tissue in which a thin layer of large scattered (d>>$\lambda$) covers a highly turbid layer of underlying tissue. Each of these layers gives rise to a different type of scattering. This two layer system represents optical properties of many human tissues with the first layer correlated with epithelium and second layer correlated with other tissue layers beneath epithelium. The upper layer is optically thin so that it does not allow multiple scattering. Small portions of incident linearly polarized light is backscattered by the particles in the upper layer. The rest of the signal penetrates to the second layer that is optically thick. Light propagating through the second layer is randomized by means of multiple scattering. This diffusive light, if not absorbed in the second layer, returns to the surface. Thus, emerging light has two contributions: one from light backscattered by the particles of the first layer, $I_b$, and the other being diffusely reflected from the second layer, $I_d$. $I_b$ has high degree of linear polarization that is parallel to the polarization of the incident light: $I_\parallel^b >> I\perp^b$. As a result of multiple scatterings in the second layer, difflusely reflected light is depolarized and $I_\parallel^d = I\perp^d$. Therefore, the residual intensity of the emerging light $I_{81} - I\perp \approx I_\parallel^b - I\perp^b$ is dominated by the contribution from the upper layer and is substantially free from both absorption and scattering from the tissue below.

Expressions (3)–(5) relate $I_\parallel - I\perp$ to the scattering amplitudes $S_1$ and $S_2$. The amplitudes depend on the wavelength of the light being scattered $\lambda = \pi/k$, the scatterer's size d and the ratio of its refractive index to that of the surrounding medium, relative refractive index n. Therefore, the spectrum of the residual intensity varies with the scatterer's size and relative refractive index. Thus, sizes and refractive indexes of the scatterers can be found by fitting the representation of the Mie theory using equations (3)–(5) to the residual intensity spectrum.

A system 10 that measures excised tissue samples in vitro is illustrated in FIG. 1. This system 10 delivers collimated polarized light on tissue 12 and separates two orthogonal polarizations of back-scattered light. The difference of these two components provides information about light scattered in the epithelial layer only. Since linearly polarized light is depolarized faster than circularly polarized light while passing through a random medium, linear polarization was used. The system provides light from a broad-band source 14 (250 W tungsten lamp, Model 66181, Oriel Instruments, Inc., Stratford, Conn.) is collimated and then refocused with a small solid angle onto the sample using a fiber 16, a lens 18 and an aperture 20. A broadband polarizer 22 linearly polarizes the beam, before it is delivered to the surface of a scattering medium through beamsplitter 24. The light beam strikes the surface of the sample with an angle ~15° relative to the normal in order to avoid specular reflectance. The diameter of the beam is 2 mm. The reflected light is collected in a narrow cone (~0.015 radian) with apertures 26 and mirror 28 and two polarizations, parallel $I_\parallel$ and orthogonal $I\perp$ to the initial polarization, are separated by a broadband polarizing beam splitter cube 28 which also acts as the analyzer (Melles Griot, Inc.). The output from this analyzer is delivered through lenses 30 and 200 μm optical fibers 32, 34 (Ocean Optics, Inc., Dunedin, Fla.) into two channels of a multichannel spectroscope 36 (quadruple spectroscope, Model SQ200, Ocean Optics, Inc., Dunedin, Fla.). This enables the spectra of both components to be measured simultaneously in the range from 300 run to 1200 or optionally in the range from 400 nm to 900 nm.

The beams are not perfectly collinear, and when they pass through the polarizer and analyzer cubes this gives rise to a small amount of distortion. Furthermore, the beamsplitter has different reflectivities for s and p polarizations. A diffusely reflective white surface was used as standard to correct for wavelength non-uniformity, and to calibrate the signals in the two channels. $I\perp(\lambda)$ and $I_\parallel(\lambda)$ were each normalized to the corresponding background spectra, $I\perp^B(\lambda)$ and $I_\parallel^B(\lambda)$ were each normalized to the corresponding background spectra, $I_\parallel^B(\lambda)$ and $I\perp^B(\lambda)$ taken with the white diffusing surface. This removes spectral non-uniformities in the light source. Thus, the experiments actually measured the normalized residual intensity, ΔI:

$$\Delta I = \frac{I_\parallel}{I_\parallel^B} - \frac{I\perp}{I\perp^B} \qquad (6)$$

Measurements on simple single- and two-layer systems were conducted to determine operational parameters. The single layer system included polystyrene beads of various sizes ranging from 0.5 μm to 10 μm (Polyscience, Inc.) embedded in de-ionized water, glycol, or glycerol. The thickness of these layers was varied so that the optical thickness τ ranged from 0.1 to 5 a photon propagating through a medium with τ=1, undergoes one scattering event on average. The beads of large sizes 4–10 μm were used to represent cell nuclei. Since the relative refractive index of the polystyrene beads in water is about 1.2 (absolute refractive index is about n=1.59) and is substantially higher than that of the cell nuclei relative to the cytoplasm which is in the range from 1.03 to 1.1, glycol ($n_a$=1.45) and glycerol ($n_a$=1.48) were used instead of water to decrease the relative refractive index of the beads and, therefore, better approximate biological conditions.

In the single layer measurements the component of the backscattered light with the same state of polarization as the incoming light (denoted by $I_{81}$) was almost 100 times larger than the component with the polarization orthogonal to the polarization of the incoming light (denoted by $I\perp$) This establishes that single scattering from large spheroidal particles preserves polarization.

In the measurements with two layer models the first layer consisted of polystyrene beads embedded in water, glycol, or glycerol and was prepared as in the single layer measurements. The second layer included a gel containing solution of $BaSO_4$ powder which provided scattering properties of the second layer and human blood. Hemoglobin content of the blood provided absorptive properties to the model. This physical model simulated epithelium and underlying tissues. Adjusting concentrations of the $BaSO_4$ powder and blood, the scattering and absorption properties, can be made similar to those of a biological tissue, since in the optical spectral region hemoglobin is known to be the major absorber.

FIGS. 2A and 2B shows spectra of the parallel $I_\parallel$ and orthogonal $I\perp$ polarized components of the light reflected from a two layer system. In this measurement, the first layer contained beads embedded in glycol. The beads had an average diameter of 4.56 μm. Standard deviation of their sizes was 0.03 μm. Optical thickness of the first layer was τ~0.8. The second layer was optically thick and its scattering and absorptive properties were comparable to those of a biological tissue. The spectrum of $I\perp$ is dominated by characteristic hemoglobin absorption bands. At the same time, characteristic spectral features of light scattered by 4.56 μm beads in the first layer, namely apparent ripple structure, and hemoglobin absorption in the second layer are seen in the spectrum of $I_\parallel$.

Figure 3A:
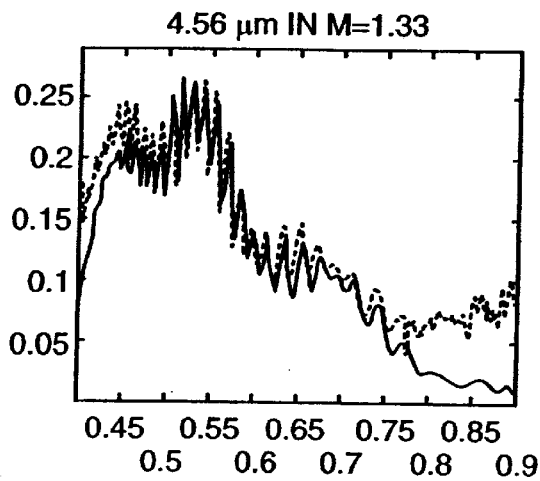
FIGS. 3A–3D illustrate differences of two polarizations for (A) 4.56 $\mu$m beads in water (relative refractive index n≈1.19), (B) 9.5 $\mu$m beads in water (n≈1.19), (C) 5.7 $\mu$m beads in glycol (n≈1.09), (D) 8.9 $\mu$m beads in glycerol (n≈1.07) where the signals (dashed lines) are in good agreement with Mie calculations (solid lines) and the absorption features of hemoglobin are completely removed.
Figure 3B:
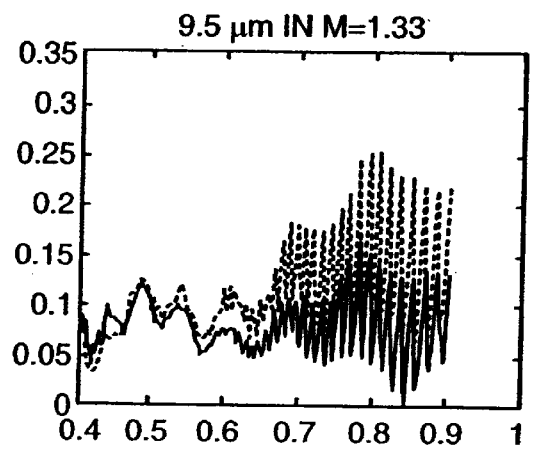

The residual spectrum ΔI is shown in FIG. 3A. No hemoglobin absorption features are seen and the diffusive background coming from the second layer was completely removed. The ripple structure characteristic of scattering from spheres is evident. The comparison with Mie theory representation for scatterers with d=4.56 μm, Δd=0.03 μm and n=1.035 correspond with the μm shown in FIG. 3B shows high degree of accuracy. The residual spectra obtained in measurements with other bead sizes (5.7 µm, 8.9 µm, and 9.5 µm) embedded in any of the media used (water, glycol, and glycerol) had no measurable diffusive background component and agreed with Mie theory. FIG. 3B shows the agreement between the theory and the measurements for 9.5 µm beads.

Figure 3C:
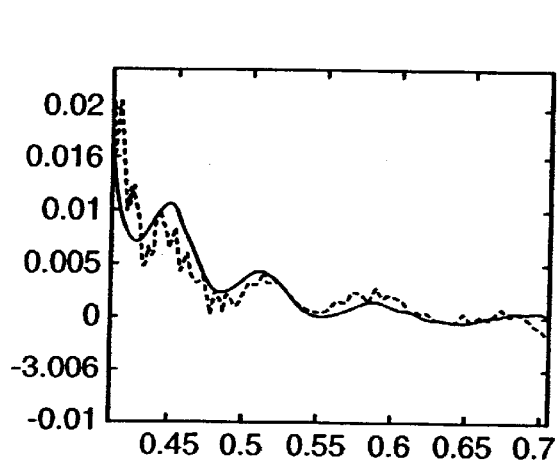
Figure 3D:
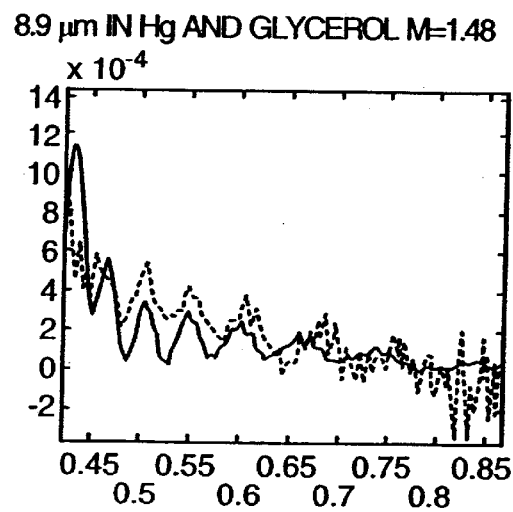

Similarly, the results of the measurements for 5.7 µm and 8.9 µm beads in glycerol and glycol are shown in FIGS. 3(C) and (D), respectively. Mie theory corresponds with the measured values in these cases as well. The high frequency ripple structure decreases as the relative refractive index gets smaller. The low frequency oscillations remain evident. Measurements showed that the instrument was able to detect signal from the bead solution of as low optical thickness as 0.05. Small disagreements seen in the spectrum can result from imperfect calibration of the instrument for the wavelength dependence of the optical elements used. The beams are not perfectly collinear and so there arises some imperfections in the polarized signals from the two channels when the beam passes through the polarizer and the analyzer elements. Further, the beam splitter used has different reflectivities for the s and the p polarized beams. However, using just a white standard, signals in the two channels were corrected for any wavelength non-uniformity and further used for calibration of signals.

Measurements with cell monolayers were conducted and the results are described in connection with FIGS. 4–6. A layer of gel containing solution of $BaSO_4$ powder and human blood under the monolayers is used to represent underlying tissue. The concentrations of the $BaSO_4$ powder and blood, were adjusted to match optical properties of the biological tissue. Three types of cells were measured: normal intestinal cells, T84 cancer colonic cells and the fibroblasts. The measurements were similar to the measurements with beads. Nuclei of cells, however, had relative refractive indexes smaller then those of beads as well as larger size distributions which substantially eliminate the ripple structure. Fitting of the observed residual spectrum to Mie theory was performed. Three parameters in the fitting procedure were average size of the nuclei, standard deviation in size (a Gaussian size distribution was assumed), and relative refractive index.

Figure 4:
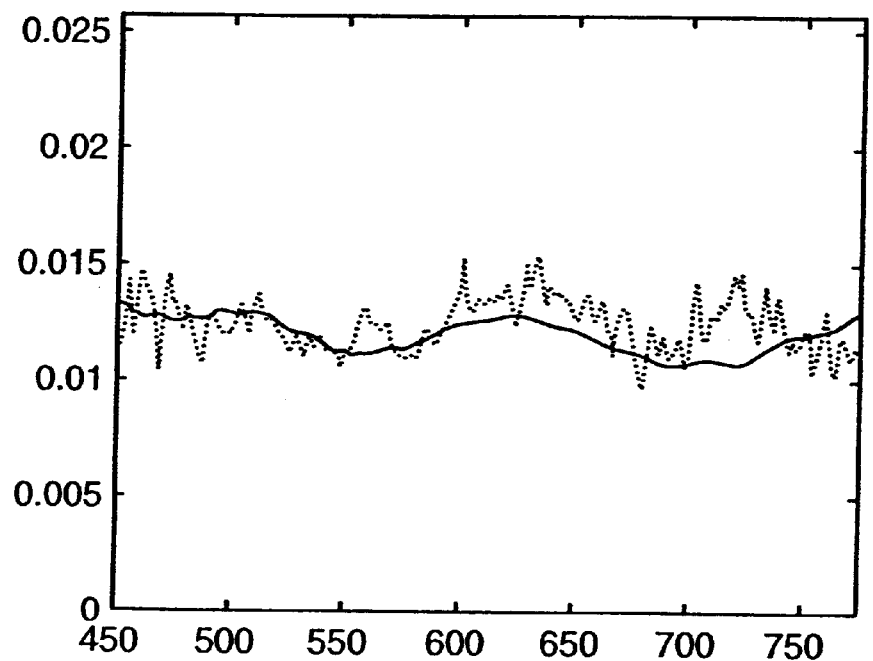
FIG. 4 is a spectrum of the polarized (residual) component of back-scattered light: experimental data vs. fit of the Mie calculations for the polarized back-scattering for T84 cancerous colonic cells where best fits provide the following sets of parameters: average size 10.2 $\mu$m, standard deviation 1.5 $\mu$m, relative refractive index 1.045, and the sizes and standard deviations are in agreement with those measured using light microscopy.
Figure 5:
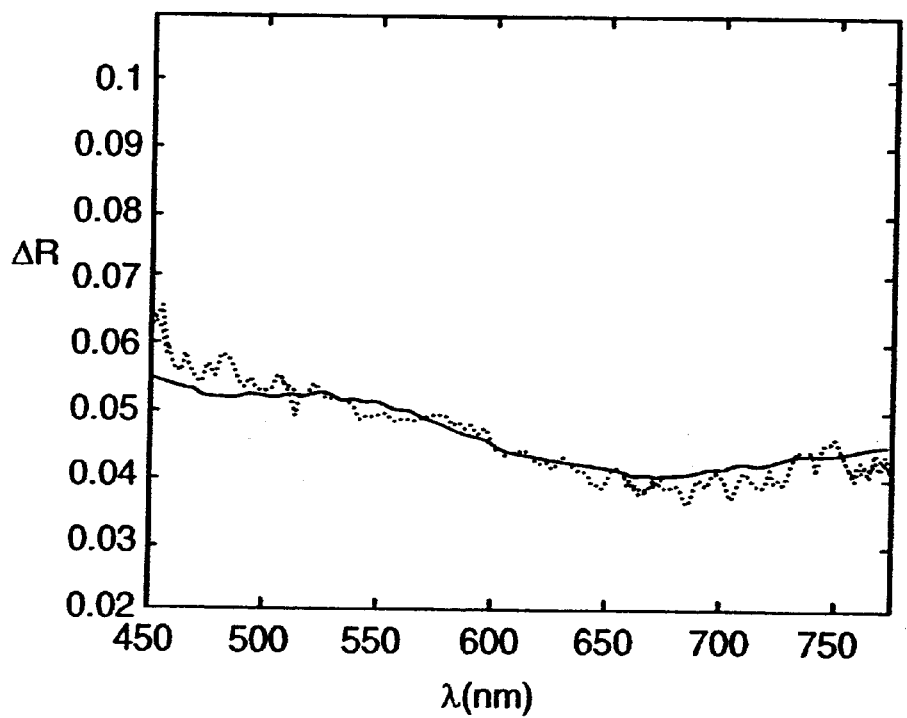
FIG. 5 is a spectrum of the polarized (residual) component of back-scattered light: experimental data vs. fit of the Mie calculations for the polarized back-scattering for normal intestinal cells where best fits provide the following sets of parameters: average size 5.0 $\mu$m, standard deviation 0.5 $\mu$m, relative refractive index 1.035, and the sizes and standard deviations are in agreement with those measured using light microscopy.

For normal intestinal cells, the best fit was obtained using d=5.0 µm, Δd=0.5 µm, and n=1.045 (FIG. 4). For the fibroblast cells, d−7.0 µm, Δd=1.0 µm, and n=1.051 were obtained. For the T84 colon cancer cells the corresponding values were d=9.8 µm, Δd=1.5 µm, and n=1.04 (FIG. 5).

In order to check these results, the distribution of the average size of the cell nuclei was measured using light microscopy. The sizes and their standard deviations were in agreement with the parameters from Mie theory. A histogram showing the size distributions obtained for the normal T84 cells are shown in FIG. 6. The accuracy of the average size is estimated to be 0.1 µm, and the accuracy in n as 0.001. Note the larger value of n obtained for cancerous cells, which is in agreement with the hyperchromaticity of cancer cell nuclei observed in conventional histopathology of stained tissue sections.

The backscattered signal can be described by Mie theory if the average size of the nuclei d standard deviation in sizes Δd, and relative refractive index n are varied. Note that in Mie theory, dependence on d and n does not always come as a (n−1)d product. Thus, the residual spectra have enough information to extract d and n simultaneously.

The size distributions for monolayers were compared to light microscopy and were in a good agreement for all three lines of cells. The accuracy of size and standard deviation extraction was approximately 0.1 µm which makes the method useful in differentiating nuclei of different cell types, including cancerous and non-cancerous cells of the same organ.

Ability to detect cell nuclear enlargement and changes in refractive index of the nucleus (which can be related to the amount of DNA and protein in the nucleus) has valuable applications in clinical medicine.

The method of tissue diagnosis can be implemented either in a diagnostic device in which light can be delivered to points on the surface of the tissue, and collected and analyzed at each of those points on the surface of the tissue, and collected and analyzed at each of those points. In an in vivo system optical fibers are used to deliver and collect light. The fiber probe can be inserted in the endoscope biopsy channel or any similar device (depending on the type of the procedure and organ under study). Polarizer and analyzer can be placed at the tip of the robe in front of the delivery and collection fibers. Such an instrument can be used during routine endoscopic procedures to detect precancerous changes in-vivo in real time.

Figure 7:
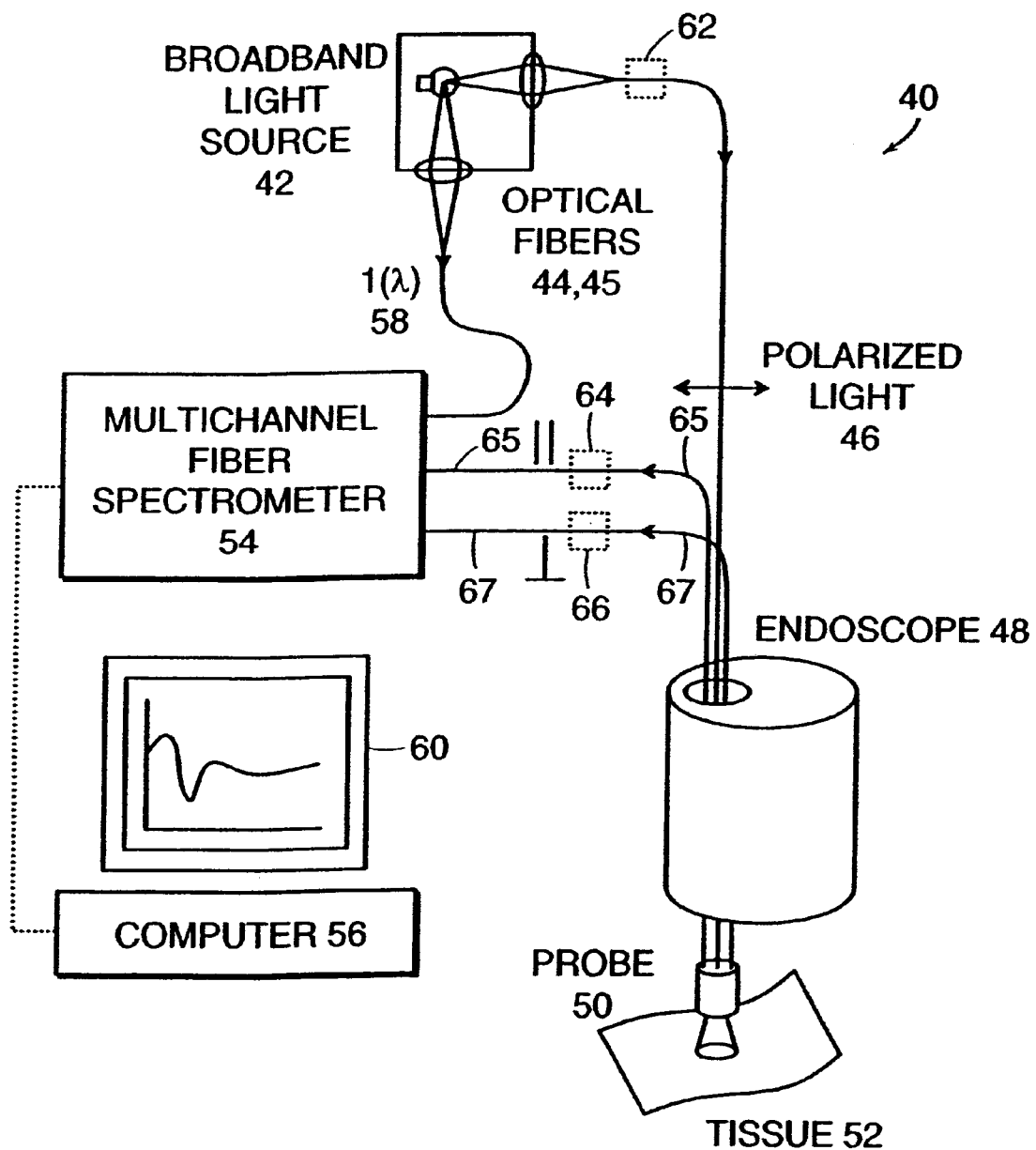
FIG. 7 schematically illustrates a fiber optic probe system for performing in vivo optical measurements of tissue in accordance with the invention.

Such a probe system 40 is shown generally in FIG. 7. This system 40 includes a broadband light source 42 that is optically coupled to a delivery fiber 44 extending through probe 50. As schematically shown in FIG. 7, the probe 50 can be inserted through a channel in an endoscope 48, however the probe 50 can be constructed to be used separately. In a preferred embodiment described hereinafter, the light from source is directed through a polarizer at the distal end of probe 50. However, in another embodiment using polarization preserving optical fibers, a polarizer 26 can be used at the proximal end of probe fiber 44 to direct polarized light 46 through the fiber. Similarly, the proximal ends of collection fibers 65, 66 can employ polarizing elements 65, 66, respectively, to transmit selected polarization components into the multichannel fiber spectrometer 54. The data can then be processed by computer 56, stored in computer 56, stored in computer memory and displayed on display 60 as needed.

Figures 8A, 8B:
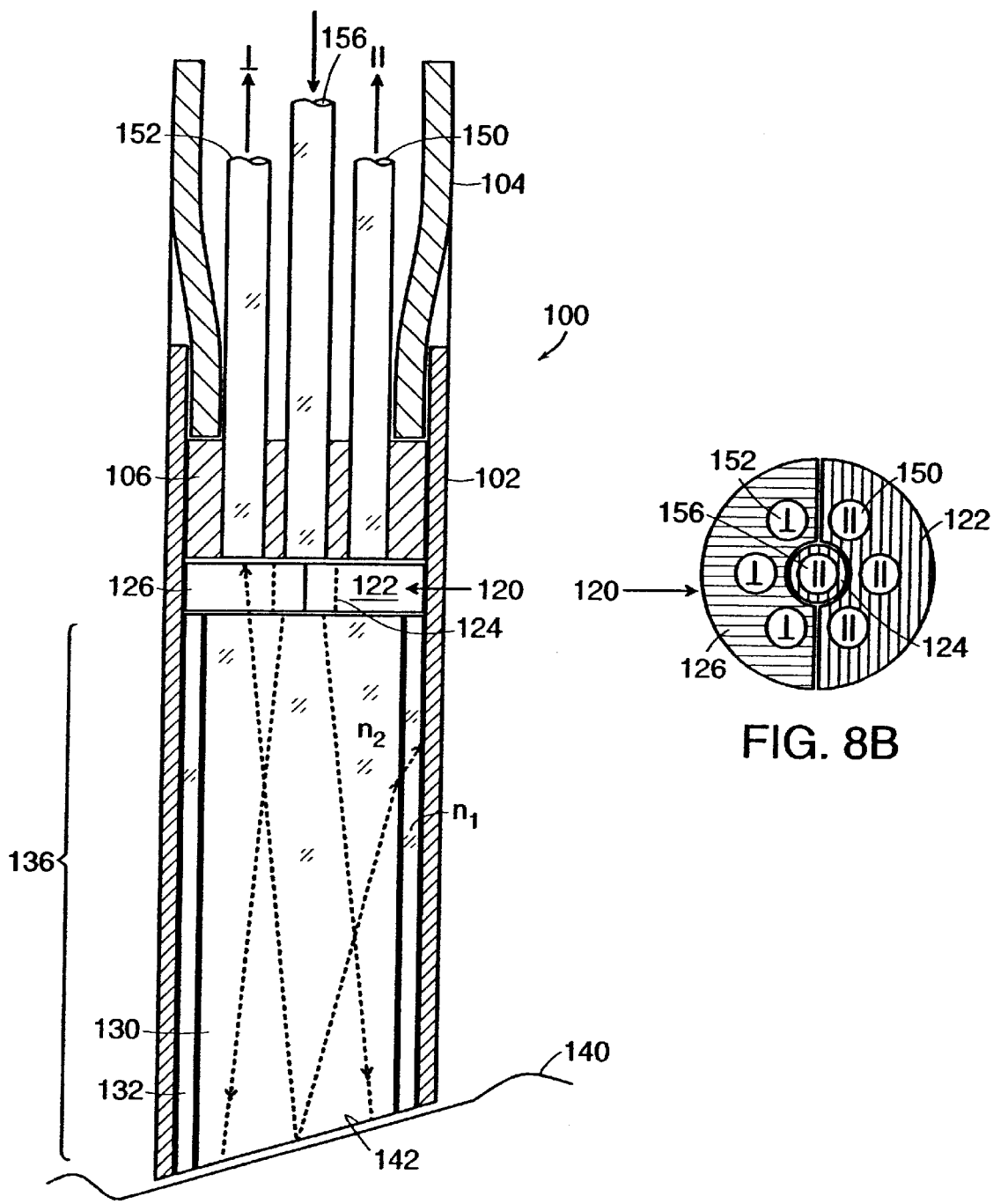
FIGS. 8A and 8B show the distal end of a probe of a preferred embodiment of the invention.

The probe system can include a fiber optic probe having a distal end incorporating polarizers as seen in FIGS. 8A and 8B.

FIGS. 8A and 8B show the distal end of a probe 100 for the use of polarized light for in vivo diagnosis. FIG. 8A shows a fiber optic device that is divided into three sections, the inner delivery fiber and two sets of collection fibers 150 and 152 that collect different polarization components. The cross-section of FIG. 8B shows fibers 156 delivering light onto the tissue 140. They have to pass through a polarizer 120 which is also seen in the cross-section view of FIG. 8B. The polarizing element is divided into at least two parts or elements 122, 126. Optical fibers 152 are arranged to collect the back reflected light from the tissue surface.

The back-scattered light has two polarization components, corresponding to the parallel and the perpendicular components to the incident light. The two are differentiated by two different birefringent analyzers shown by two sectioned ring elements 122, 126. A first element 122 allows the parallel component to pass through while the second element 126 allows perpendicular component. A portion of element 122 polarizes light exiting fiber 156. As the fibers have low numerical apertures to collect light over very small angles, it is necessary to extend the distance 136 between the fiber ends and the aperture surface 142 opening to the tissue surface 140. It can be as long as 5 mm. To avoid spurious internal reflections a glass block 130 is shown having refractive index $n_2$ larger than that of the shield 132 with refractive index $n_1$. The shield 132 can be coated with an absorbing element so that light hitting the boundaries is refracted out and then absorbed by the absorbing coating on the inner wall of the shield 132. The glass element 130 is bevelled to avoid specular reflections from the tissue surface as it is described to increase the relative signal strength of the back-scattering. The light having the two orthogonal polarizations is separated and coupled to two spectrometer channels for detection and analysis.

Figure 9A:
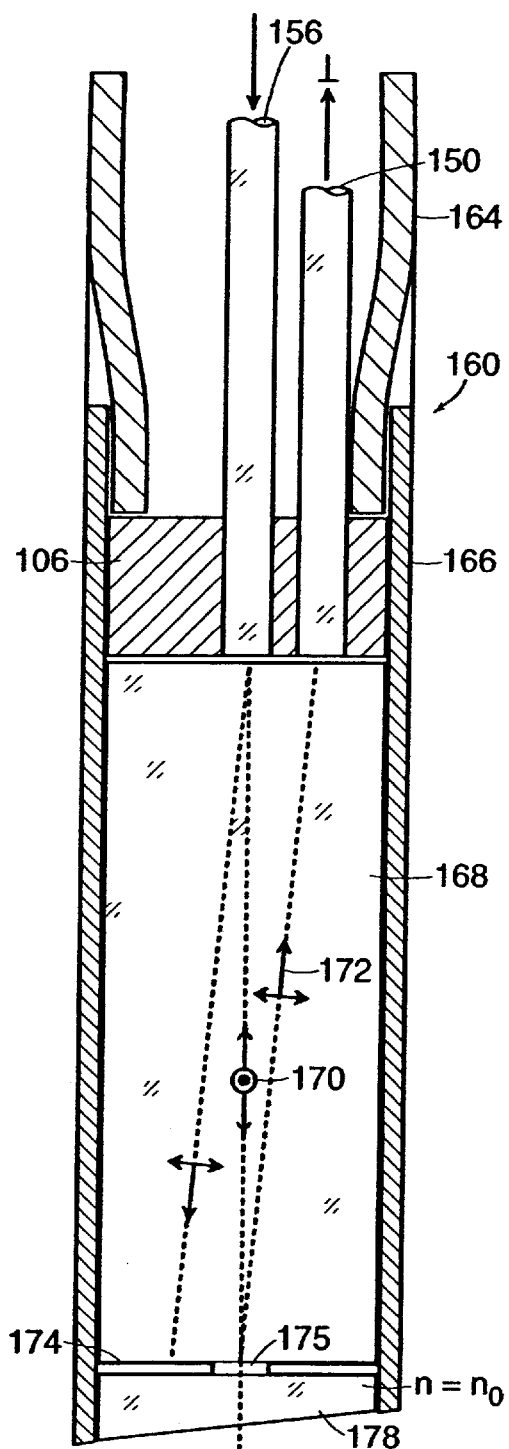
FIGS. 9A–9C illustrate another preferred embodiment of a fiber optic probe in accordance with the invention.
Figure 9B:
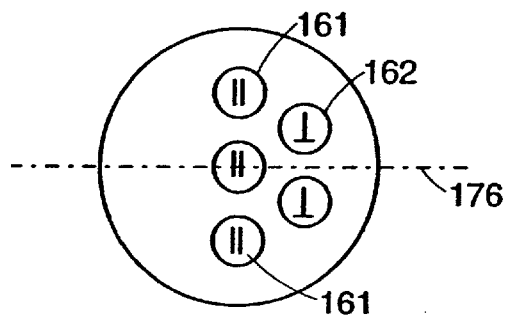
Figure 9C:
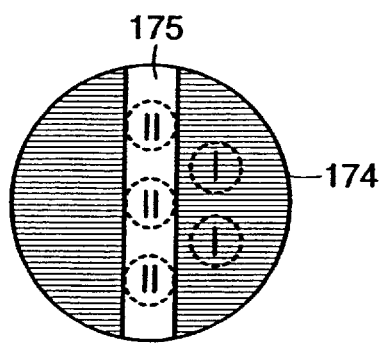

Another preferred embodiment of a fiber optic probe 160 is illustrated in FIGS. 9A–9C. In this embodiment, delivery 156 and collection 162 fibers are housed in flexible tube 164 that is attached to a distal annular housing 166. Housing 166 includes a fiber retainer 106 and a polarizer 168 which can be a birefringent crystal such as calcite, quartz or sapphire. Delivery fiber 156 delivers light from source 42 to polarizer 168 which delivers ordinary ray 170 through aperture 175 and window 178. Light returning through aperture 175 has ordinary 170 and extraordinary 172 components. The perpendicular component is collected by fibers 162 and the parallel component is collected by fibers 161. The delivery fiber 156 is positioned along the optical axis 176 of the crystal 168. Fibers 161, 156 are aligned along the aperture 175 of absorbing plate 178.

While this invention has been particularly shown and described with references to preferred embodiments thereof, it will be understood by those skilled in the art that various changes in form and details may be made therein without departing from the spirit and scope of the invention as defined by the appended claims.

The claims should not be read as limited to the described order or elements unless stated to that effect. Therefore, all embodiments that come within the scope and spirit of the following claims and equivalents thereto are claimed as the invention.

What is claimed:

1. A fiber optic probe for measuring a surface layer of tissue comprising:
    a fiber optic cable optically coupled to a light source, the fiber optic cable delivering light having a plurality of wavelengths from the light source onto the tissue of a patient;
    a polarizer optically coupled to the fiber optic cable to polarize incident light directed through the cable onto the tissue;
    an analyzer to separate polarization components of light returning from the tissue through the fiber optic cable, the returning light having a component that is periodic as a function of wavelength; and
    a detector system that is optically coupled to the analyzer such that the detector system detects the separated polarization components of light including the periodic component, the detector system generating spectral data to determine a size of a structure in the tissue.

2. The probe of claim 1, wherein the polarizer is positioned at a distal end of the fiber optic cable.

3. The probe of claim 1, wherein the analyzer is positioned at a distal end of the fiber optic cable.

4. The probe of claim 1, further comprising an endoscope having a channel through which the probe is inserted.

5. The probe of claim 1, wherein the analyzer comprises a polarizing beam splitter.

6. The probe of claim 1, further comprising a processor that determines a size of tissue cells within the tissue.

7. The probe of claim 1, wherein the detector system generates a second spectrum with detected light, the second spectrum including wavelengths in the range of 300 nm to 1200 nm.

8. The probe of claim 1, wherein the source comprises a broadband light source and a filter wheel.

9. The probe of claim 1, further comprising a spectrometer optically coupled to the fiber optic probe.

10. A fiber optic light delivery and collection system for measuring a surface layer of tissue comprising:
    a fiber optic probe housing having a proximal end and a distal end;
    at least one central delivery fiber disposed in the fiber optic probe housing, the central delivery fiber coupled to a source through a fiber optic cable, the source providing, a plurality of wavelengths, and a polarizer coupled to the central delivery fiber to polarize incident light directed through the fiber optic cable onto the tissue;
    at least one off-center collection fiber disposed in the fiber optic probe housing to collect light returning from the tissue having at least two different polarization components, one component that is periodic as a function of wavelength;
    an analyzer coupled to the at least one off-center collection fiber to separate the polarization components of light returning from the tissue; and
    a detector system that is optically coupled to the analyzer such that the detector system detects the separated polarization components of light including the periodic component, the detector system generating a spectrum of light having the polarization of the incident light to determine a size of a structure in the tissue.

11. The fiber optic light delivery and collection system of claim 10, wherein the polarizer is positioned at a distal end of the fiber optic cable.

12. The fiber optic light delivery and collection system of claim 10, wherein the polarizer comprises birefringent crystalline material.

13. The fiber optic light delivery and collection system of claim 10, wherein the analyzer is positioned at a distal end of the fiber optic cable.

14. The fiber optic light delivery and collection system of claim 10, further comprising an endoscope having a channel through which the at least one central delivery fiber and at least one off-center collection fiber is inserted.

15. The fiber optic light delivery and collection system of claim 10, wherein the analyzer comprises a polarizing beam splitter.

16. The fiber optic light delivery and collection system of claim 10, further comprising the detector system determining a size of tissue cells within the tissue.

17. The fiber optic light delivery and collection system of claim 10, wherein the detector system generating a second spectrum with detected light, the second spectrum including wavelengths in the range of 300 nm to 1200 nm.

18. The fiber optic light delivery and collection system of claim 10, wherein the source comprises a broadband light source and a filter wheel.

19. The fiber optic light delivery and collection system of claim 10, further comprising a spectrometer optically coupled to the analyzer.

* * * * *